(12) United States Patent
Kang (10) Patent No.: US 12,420,119 B1
(45) Date of Patent: Sep. 23, 2025

(54) STRUCTURE OF SURGICAL DEVICE FOR IRRADIATING FOCUSED ULTRASOUND TO MULTIPLE DEPTHS AND SURGICAL METHOD USING THE SAME

(71) Applicant: Shenb Co., Ltd., Seoul (KR)

(72) Inventor: Sunyoung Kang, Seoul (KR)

(73) Assignee: Shenb Co., Ltd., Seoul (KR)

( * ) Notice: Subject to any disclaimer, the term of this patent is extended or adjusted under 35 U.S.C. 154(b) by 0 days.

(21) Appl. No.: 18/937,711

(22) Filed: Nov. 5, 2024

(30) Foreign Application Priority Data

Oct. 18, 2024 (KR) .......................... 10-2024-0142928

(51) Int. Cl.
*A61N 7/00* (2006.01)

(52) U.S. Cl.
CPC ........ *A61N 7/00* (2013.01); *A61N 2007/0091* (2013.01)

(58) Field of Classification Search
CPC .......................... A61N 7/00; A61N 2007/0091
See application file for complete search history.

(56) References Cited

FOREIGN PATENT DOCUMENTS

| KR | 10-1712024 B1 | 3/2017 |
|---|---|---|
| KR | 10-2018-0136426 A | 12/2018 |
| KR | 10-2024-0140667 A | 9/2024 |
| KR | 10-2024-0145337 A | 10/2024 |

*Primary Examiner* — Jason M Ip
(74) *Attorney, Agent, or Firm* — Bridgeway IP Law Group, PLLC; Jihun Kim (57) ABSTRACT

According to an exemplary embodiment, a structure of a surgical device for irradiating focused ultrasound to multiple depths includes: a motor equipped with a rotating shaft; a ball screw rotating by power of the motor, having a first external screw thread engraved on an outer side, and having an accommodation groove formed in a longitudinal direction on a portion of the outer side; and a ball nut having an internal screw thread engraved on an inner side that meshes with the first external screw thread when the ball screw is penetrated, and moving linearly by following the rotation of the ball screw.

15 Claims, 9 Drawing Sheets

STRUCTURE OF SURGICAL DEVICE FOR IRRADIATING FOCUSED ULTRASOUND TO MULTIPLE DEPTHS AND SURGICAL METHOD USING THE SAME

CROSS-REFERENCE TO RELATED APPLICATIONS

This application claims the priority of Korean Patent Application No.10-2024-0142928 filed on Oct. 18, 2024, in the Korean Intellectual Property Office, the disclosure of which is incorporated herein by reference.

BACKGROUND

Field

The present disclosure relates to a structure of a surgical device for irradiating focused ultrasound to multiple depths and a surgical method using the same, and more particularly, to a structure of a surgical device capable of simply irradiating focused ultrasound to a skin of a subject to multiple depths and a surgical method using the same.

Description of the Related Art

Typically, there was a motor structure for linear movement of a transducer. However, in order to implement the up/down movement of the transducer, a separate actuator such as a solenoid or a motor for depth adjustment of the transducer, and a sensor for measuring the up/down movement distance of the transducer in the case of a piezo or ball screw method, etc., need to be additionally configured, which may lead to the problem of complicating the configuration of the device in which the transducer is configured.

In addition, there is a conventional surgical method using a surgical device for irradiating focused ultrasound to a skin of a subject to multiple depths. In this conventional surgical method, when the focused ultrasound is irradiated to the skin of the subject to different depths, a transducer assembly first moves up/down to a first depth, the transducer horizontally linearly irradiates the focused ultrasound, the transducer assembly is adjusted up/down to a second depth, and then the transducer horizontally linearly irradiates the focused ultrasound to the second depth, thereby improving the skin condition of the subject. However, since a plurality of motors is required to move the transducer assembly up/down and to horizontally linearly irradiate the focused ultrasound from the transducer, there is a problem that the configuration of the surgical device and the process of the surgical method become complicated.

Accordingly, there is a need for research on a surgical device and surgical method capable of simply irradiating focused ultrasound to a skin of a subject to multiple depths.

RELATED ART DOCUMENT

Patent Document

Korean Patent No. 10-1712024 (registered on Feb. 24, 2017)

SUMMARY

An object to be achieved by the present disclosure is to provide a structure of a surgical device for irradiating focused ultrasound to multiple depths, which can adjust an irradiation depth of the focused ultrasound by implementing up/down vertical movement of a transducer assembly while omitting a configuration of an actuator for horizontal movement and up/down vertical movement, and can set the irradiation depth of the focused ultrasound without adding a separate sensor.

Another object to be achieved by the present disclosure is to provide a structure of a surgical device capable of irradiating focused ultrasound to a skin of a subject to multiple depths in a form in which one cycle of a sine wave is repeated by moving a transducer assembly horizontally and up/down vertically while accommodating a conventional surgical method, and a surgical method using the same.

However, objects of the present disclosure are not limited to the above-described objects. That is, other objects that are not described may be obviously understood by those skilled in the art to which the present disclosure pertains from the following description.

According to an exemplary embodiment, a structure of a surgical device for irradiating focused ultrasound to multiple depths may include: a motor equipped with a rotating shaft; a ball screw rotating by power of the motor, having a first external screw thread engraved on an outer side, and having an accommodation groove formed in a longitudinal direction on a portion of the outer side; a ball nut having an internal screw thread engraved on an inner side that meshes with the first external screw thread when the ball screw is penetrated, and moving linearly by following the rotation of the ball screw; a first gear having a protrusion formed on an inner side that is fitted into the accommodation groove when the ball screw is penetrated to follow the rotation of the ball screw, engaging with the ball nut to follow the linear movement of the ball nut, and having a second external screw thread engraved on an outer diameter; a second gear having a third external screw thread engraved on an outer diameter and meshing with the second external screw thread to follow the rotation of the first gear, and having an eccentric shaft provided asymmetrically; a first transducer assembly moving horizontally by linear movement of the ball nut and the first gear, and vertically moving up/down to irradiate the focused ultrasound to the multiple depths; and a housing formed with a horizontal long hole that is coupled with the first transducer assembly while boxing the ball nut, the first gear, and the second gear and converts rotational energy of the second gear into up/down movement energy for vertically moving the first transducer assembly up/down while interfering with the rotation of the second gear by interlocking with the eccentric shaft.

The first transducer assembly may move horizontally to one side by a pitch distance of the ball screw based on the fact that the ball nut and the first gear linearly move to one side by the pitch distance of the ball screw when the ball screw rotates one turn in one direction.

While the first transducer assembly may move horizontally to one side by the pitch distance of the ball screw, the first transducer assembly may repeat the up/down vertical movement from one point of a maximum upper point and a maximum lower point toward the other point in a form that one cycle of a sine wave is repeated through the up/down movement energy converted from the rotational energy of the second gear based on the interlocking between the eccentric shaft and the horizontal long hole.

The first transducer assembly may repeat the up/down vertical movement from a starting position which is a midpoint between the maximum upper point and the maximum lower point before a treatment of a subject starts, and then returns to the starting position when the treatment of the subject ends.

The structure may further include an up/down vertical movement auxiliary means assisting the up/down movement of the first transducer assembly.

The up/down vertical movement auxiliary means may be connected to the second gear to receive the rotational energy from the second gear, and convert the rotational energy of the second gear for vertically moving the first transducer assembly up/down into up/down movement energy by interlocking with the housing.

The housing may have a horizontal long hole additionally formed on a side portion opposite to a side portion where the horizontal long hole is formed.

The up/down vertical movement auxiliary means may include: a rotating shaft connected to the second gear to receive the rotational energy from the second gear; a rotary member connected to the rotating shaft to receive the rotational energy from the second gear through the rotating shaft; and an auxiliary eccentric shaft asymmetrically provided on the rotary member, and penetrating through the horizontal long hole additionally formed in the housing to convert the rotational energy of the rotary member into the up/down movement energy while interfering with the rotation of the rotary member when the rotary member rotates by the rotational energy of the second gear.

The surgical device may be a cartridge and a handpiece to which the structure is applicable.

When the structure is applied to the cartridge, the first transducer assembly may perform a role of a traction shaft for moving a transducer that irradiates the focused ultrasound using driving force of a motor built into the handpiece, and the transducer may be built into the cartridge, coupled with the first transducer assembly, and follow the horizontal movement and the up/down vertical movement of the first transducer assembly to move horizontally and vertically move up/down and irradiate the focused ultrasound to the multiple depths.

When the structure is applied to the handpiece, the first transducer assembly may be coupled with the second transducer assembly included in the cartridge while performing a role of a first traction shaft for moving the transducer that irradiates the focused ultrasound using the driving force of the motor built into the handpiece, the second transducer assembly may perform a role of a second traction shaft for moving the transducer by following the horizontal movement and the up/down vertical movement of the first transducer assembly, and the transducer may be built into the cartridge, coupled with the second transducer assembly, and follow the horizontal movement and the up/down vertical movement of the second transducer assembly to move horizontally and vertically move up/down and irradiate the focused ultrasound to the multiple depths.

The cartridge may have a penetration opening, through which the focused ultrasound passes, formed on a contact surface that contacts the skin of the subject so that the focused ultrasound generated from the transducer is irradiated to the skin of the subject.

The handpiece may have an engaging opening having a movable diameter, through which the first transducer assembly or the second transducer assembly penetrates, formed on a binding surface with the cartridge so that the first transducer assembly moves and is coupled with the second transducer assembly.

The housing may have a vertical long hole formed in the side portion, through which the ball screw penetrates, to prevent the interference of the ball screw during the up/down vertical movement of the first transducer assembly.

According to an exemplary embodiment, a surgical method using a structure of a surgical device for irradiating focused ultrasound to multiple depths may include: a) rotating a ball screw one turn in one direction by the power of a motor equipped with a rotating shaft; b) moving a ball nut linearly along the ball screw and allowing a first gear engaging with the ball nut to follow the linear movement of the ball nut so that the ball nut and the first gear linearly move to one side by a pitch distance of the ball screw; c) simultaneously with step b), rotating the first gear by following the rotation of the ball screw and rotating a second gear meshed with the first gear by following the rotation of the first gear; d) simultaneously with step c), converting rotational energy of the second gear into up/down movement energy for vertically moving up/down a first transducer assembly 160 while an eccentric shaft of the second gear and a horizontal long hole of the housing interfere with the rotation of the second gear; and e) horizontally moving the first transducer assembly along the housing while repeating steps a to d) and vertically moving the first transducer assembly up/down to irradiate the focused ultrasound to the multiple depths by the up/down movement energy.

Effect of the Invention

According to the present disclosure, it is possible to provide the surgical device of a simple configuration including the structure capable of adjusting the irradiation depth of the focused ultrasound by implementing the up/down vertical movement of the transducer assembly while omitting the configuration of the actuator for horizontal movement and up/down vertical movement and setting the irradiation depth of the focused ultrasound without adding the separate sensor.

In addition, according to the present disclosure, by irradiating the focused ultrasound to the skin of the subject to multiple depths while the transducer assembly moves horizontally and up/down vertically while accommodating the conventional surgical method, it is possible to improve the skin condition of the subject based on various surgical methods.

However, effects which can be achieved by the present disclosure are not limited to the above-described effects. That is, other objects that are not described may be obviously understood by those skilled in the art to which the present disclosure pertains from the following description.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

Hereinafter, exemplary embodiments of the present disclosure will be described in detail with reference to the accompanying drawings so that those skilled in the art to which the present disclosure pertains may easily practice the present disclosure. However, description of the present disclosure is only an exemplary embodiment for structural or functional description, and therefore the scope of the present disclosure should not be construed as limited to exemplary embodiments described in the text. That is, since the exemplary embodiments may be variously modified and may have various forms, the scope of the present disclosure should be construed as including equivalents capable of realizing the technical idea. In addition, a specific exemplary embodiment is not construed as including all the objects or effects presented in the present disclosure or only the effects, and therefore the scope of the present disclosure should not be understood as being limited thereto.

The meaning of the terms described in the present specification should be understood as follows.

Terms such as "first" and "second" are intended to distinguish one component from another component, and the scope of the present disclosure should not be limited by these terms. For example, a first component may be named a second component and the second component may also be similarly named the first component. It is to be understood that when one element is referred to as being "connected to" another element, it may be connected directly to or coupled directly to another element or be connected to another element, having the other element intervening therebetween. On the other hand, it is to be understood that when one element is referred to as being "connected directly to" another element, it may be connected to or coupled with another element without the other element intervening therebetween. Meanwhile, other expressions describing a relationship between components, that is, "between", "directly between", "neighboring to", "directly neighboring to" and the like, should be similarly interpreted.

It should be understood that the singular expression includes the plural expression unless the context clearly indicates otherwise, and it will be further understood that the terms "comprise" or "have" used in this specification, specify the presence of stated features, numerals, steps, operations, components, parts, or a combination thereof, but do not preclude the presence or addition of one or more other features, numerals, steps, operations, components, parts, or a combination thereof.

Unless defined otherwise, all the terms used herein including technical and scientific terms have the same meaning as meanings generally understood by those skilled in the art to which the present disclosure pertains. It should be understood that the terms defined by the commonly used dictionary are identical with the meanings within the context of the related art, and they should not be ideally or excessively formally defined unless the context clearly dictates otherwise.

Structure of Surgical Device

Hereinafter, a configuration of a preferred exemplary embodiment of a structure 100 of a surgical device for irradiating focused ultrasound to multiple depths according to the present disclosure will be described in detail with reference to the accompanying drawings.

Figure 1:
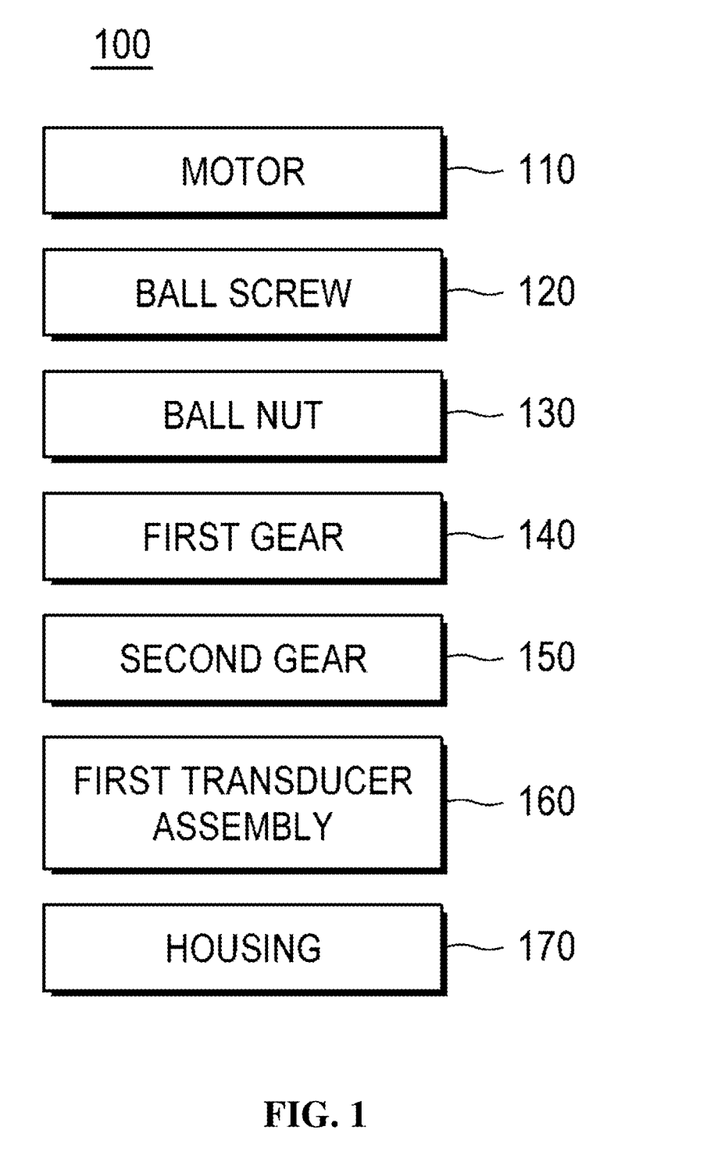
FIG. 1 is a block diagram illustrating components constituting a structure of a surgical device for irradiating focused ultrasound to multiple depths according to an exemplary embodiment of the present disclosure.

FIG. 1 is a block diagram illustrating components constituting a structure of a surgical device for irradiating focused ultrasound to multiple depths according to an exemplary embodiment of the present disclosure.

Referring to FIG. 1, the structure 100 of the present disclosure may include a motor 110, a ball screw 120, a ball nut 130, a first gear 140, a second gear 150, a first transducer assembly 160, and a housing 170 so that the surgical device may irradiate the focused ultrasound to a skin of a subject to multiple depths.

In an exemplary embodiment, the surgical device is described as irradiating the focused ultrasound to the skin of the subject, but this is not limited thereto, and the focused ultrasound may be replaced with a laser according to the purpose of the skin treatment.

In addition, components 110 to 170 of the structure 100 may be built into the surgical device, and may be implemented in the form of examples illustrated in FIGS. 2 to 5 to be built into the surgical device.

Figure 2:
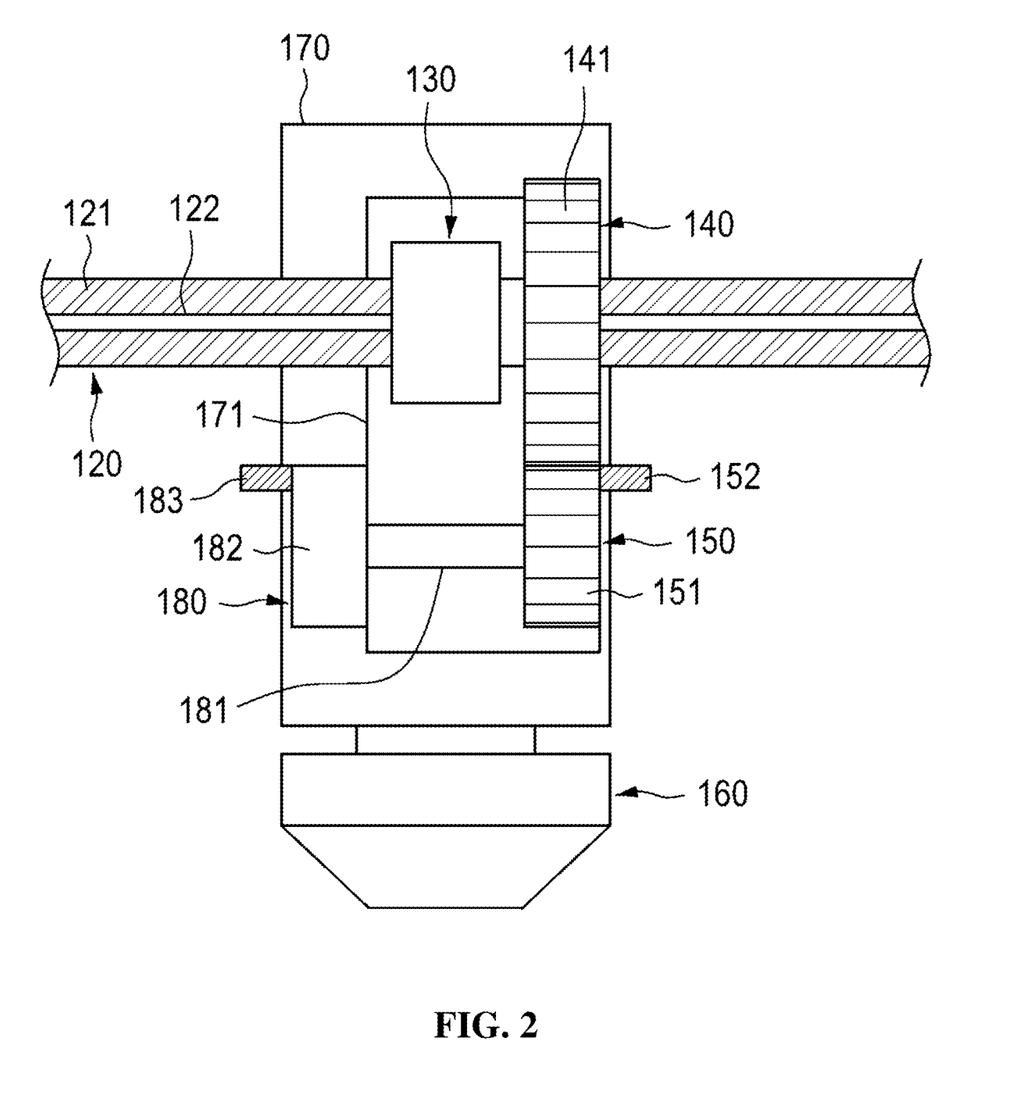
FIG. 2 is a diagram schematically illustrating the structure of a surgical device for irradiating focused ultrasound to multiple depths according to an exemplary embodiment of the present disclosure.
Figure 3:
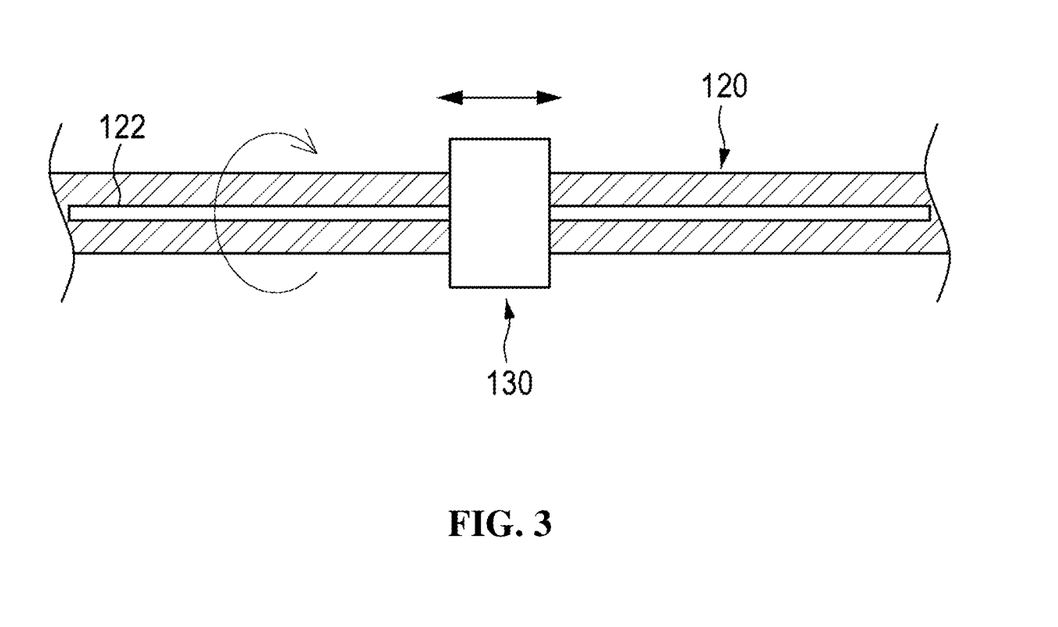
FIG. 3 is a diagram for describing the relationship between a ball screw and a ball nut illustrated in FIG. 2.
Figure 4:
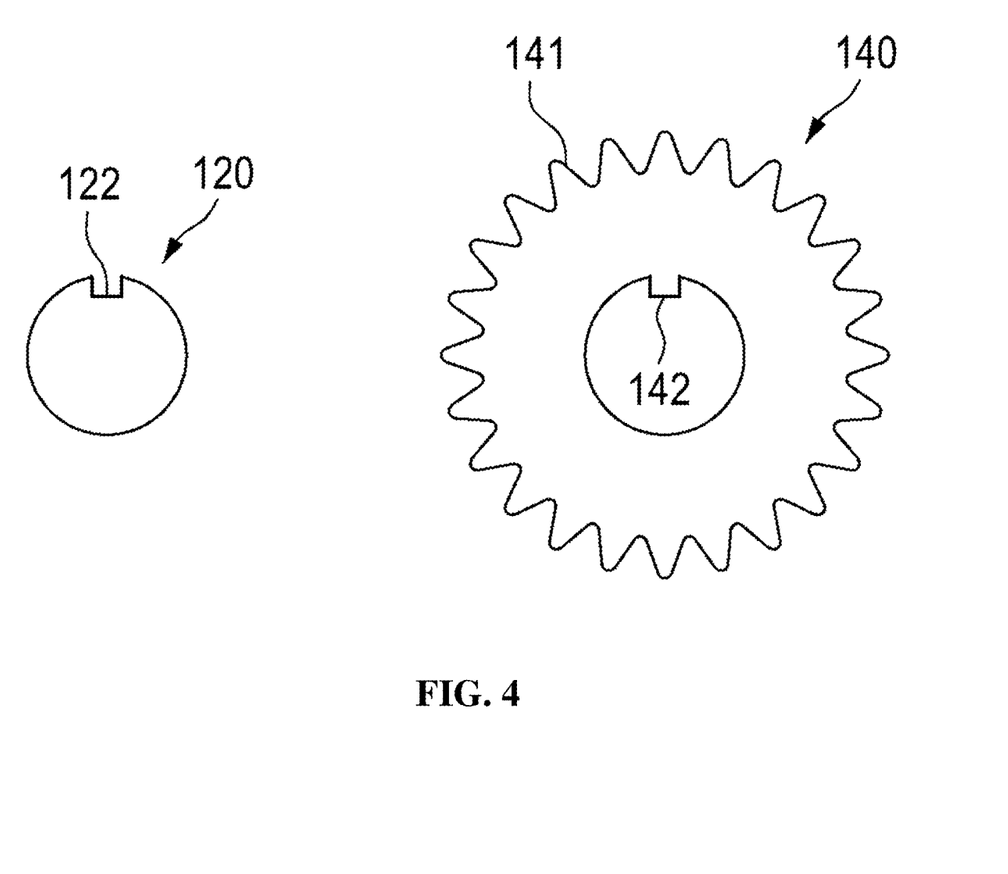
FIG. 4 is a diagram for describing the relationship between the ball screw and a first gear illustrated in FIG. 2.
Figure 5:
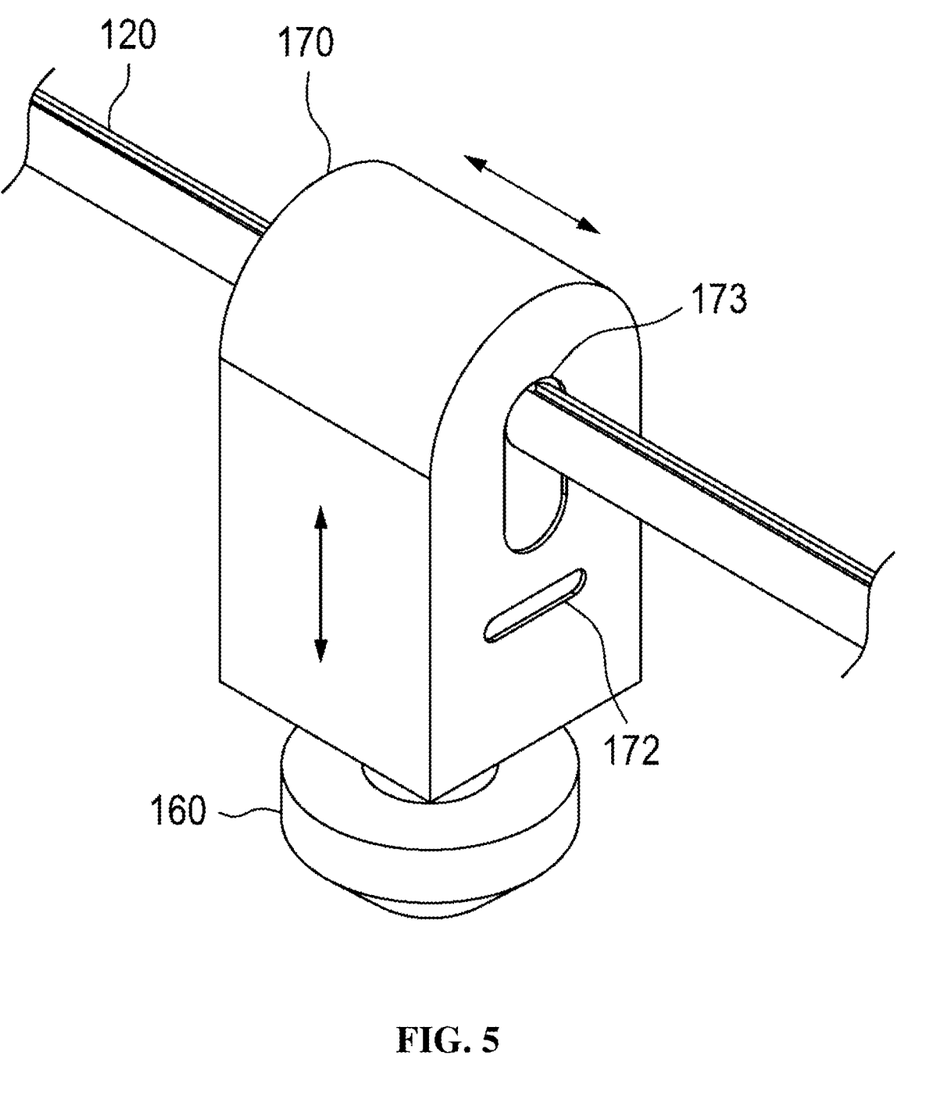
FIG. 5 is a perspective view of a structure according to an exemplary embodiment of the present disclosure.
Figure 6A:
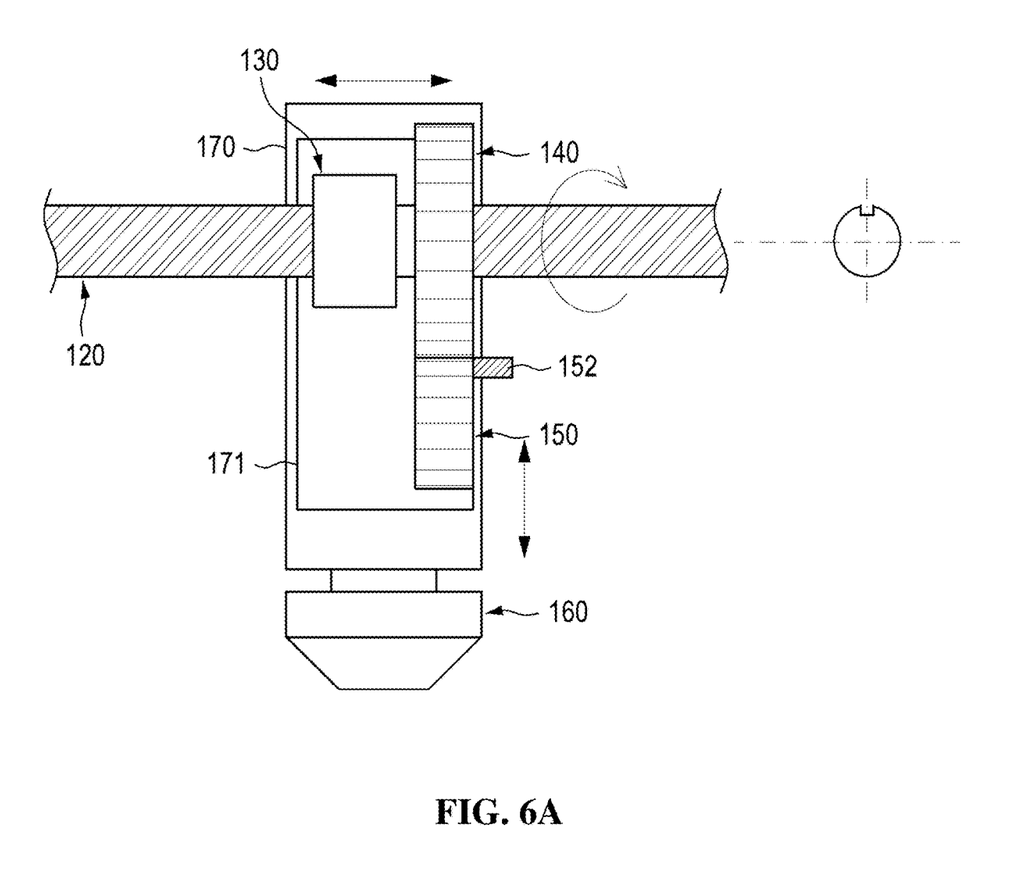
FIGS. 6A to 6C are diagrams for describing a horizontal movement and an up/down vertical movement of a first transducer assembly.
Figure 6B:
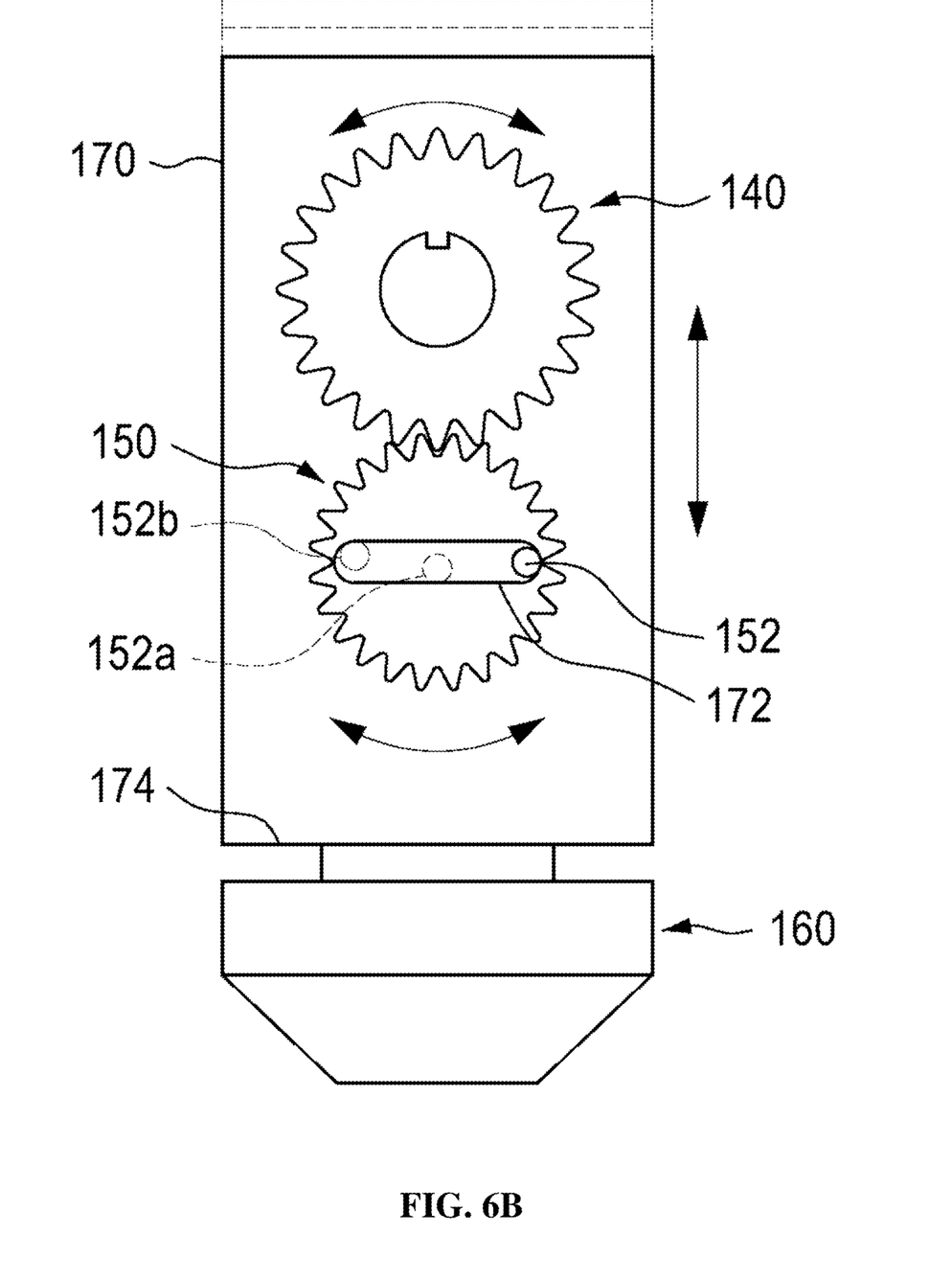
Figure 6C:
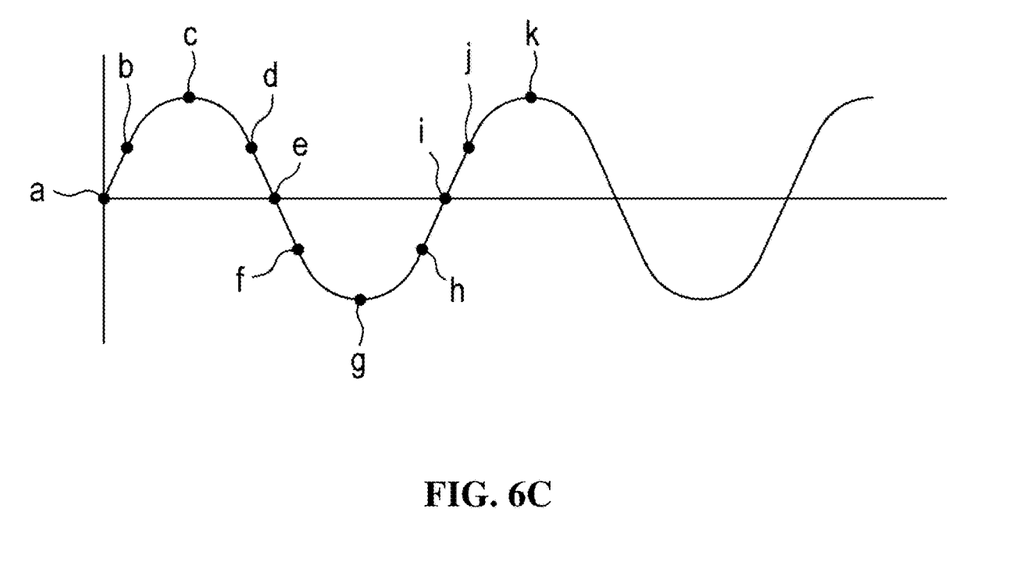

FIG. 2 is a diagram schematically illustrating the structure of a surgical device for irradiating focused ultrasound to multiple depths according to an exemplary embodiment of the present disclosure, FIG. 3 is a diagram for describing the relationship between a ball screw and a ball nut illustrated in FIG. 2, FIG. 4 is a diagram for describing the relationship between the ball screw and a first gear illustrated in FIG. 2, FIG. 5 is a perspective view of a structure according to an exemplary embodiment of the present disclosure, and FIGS. 6A to 6C are diagrams for describing a horizontal movement and an up/down vertical movement of a first transducer assembly.

Referring to FIGS. 2 to 6, the motor 110 of the present disclosure is an electric motor built into the surgical device for improving a skin condition of a subject by irradiating the focused ultrasound to the skin of the subject. Although not illustrated in the drawings, a rotating shaft (not illustrated) for transmitting power to the ball screw 120 may be provided on one side.

As illustrated in FIG. 2, the ball screw 120 of the present disclosure is a screw shaft partially disposed inside the housing 170, and may receive power from the motor 110 and rotate in one direction for horizontal movement and up/down vertical movement of the first transducer assembly 160.

In addition, the ball screw 120 may go through a rolling and cutting (lathe processing) process so that a first external screw thread 121 may be engraved on the outer side.

In addition, the ball screw 120 may go through an engraving process so that an accommodation groove 122 may be formed longitudinally on a portion of the outer side.

That is, the ball screw 120 may be a screw shaft that goes through a process for engraving the first external screw thread 121 and forming the accommodation groove 122.

In addition, the ball screw 120 may be partially disposed inside the housing 170 by penetrating through a vertical long hole 173 of the housing 170 as illustrated in FIG. 5.

The ball nut 130 of the present disclosure is disposed inside the housing 170 as illustrated in FIG. 2, and although not illustrated in the drawings, goes through the rolling and cutting (lathe processing) process so that an internal screw thread (not illustrated) may be engraved on the inner side.

In addition, the ball screw 120 penetrates through the ball nut 130, and the internal screw thread (not illustrated) engages with the first external screw thread 121 when the ball screw 120 penetrates through the ball nut 130, so the ball nut 130 may move linearly by following the rotation of the ball screw 120.

The first gear 140 of the present disclosure is disposed inside the housing 170 as illustrated in FIG. 2, and goes through gear cutting, hobbing, and forming processes so that a second external screw thread 141 may be engraved on the outer side.

The second external screw thread 141 of the present disclosure is named the same as screw threads engraved on an outer side of the ball screw 120 and an inner side of the ball nut 130, but in reality, means a gear tooth that is a protruding portion on an outer side of the gear for power transmission.

In addition, the first gear 140 may have a protrusion 142 that can be fitted into the accommodation groove 122 and is formed on the inner side opposite to the outer side on which the second external screw thread 141 is engraved.

The ball screw 120 penetrates through the first gear 140, and the first gear may follow the rotation of the ball screw 120 by allowing the protrusion 142 to be fitted into the accommodation groove 122 based on the time when the ball screw 120 penetrates through the first gear 140.

In addition, the first gear 140 engages with the ball nut 130 to follow the linear movement of the ball nut 130.

That is, when the first gear 140 engages with the ball nut 130 while following the rotation of the ball screw 120 and the linear movement of the ball nut 130, it may move linearly (move horizontally) to one side by a pitch distance of the ball screw 120 together with the ball nut 130 based on the time when the ball screw 120 rotates one turn in one direction, and at the same time rotate in one direction.

The second gear 150 of the present disclosure may go through the gear cutting, hobbing, and forming processes so that a third external screw thread 151 may be engraved on the outer side.

The third external screw thread 151 may mesh with the second external screw thread 141 so that the second gear 150 follows the rotation of the first gear 140.

Like the second external screw thread 141, the third external screw thread 151 means a gear tooth that is a protruding portion on the outer side of the gear.

The second gear 150 is boxed together with the ball nut 130 and the first gear 140 through the box module 171 so it is disposed inside the housing 170 as illustrated in FIG. 2, and thus, may move horizontally by following the linear movement of the ball nut 130.

In addition, the second gear 150 may be equipped with an eccentric shaft 152 as illustrated in FIG. 2 for the up/down vertical movement of the first transducer assembly 160.

The eccentric shaft 152 of the present disclosure penetrates through a horizontal long hole 172 of the housing 170, which will be described later, and may convert the rotational energy received from the first gear 140 to the second gear 150 into the up/down movement energy while interfering with the rotation of the second gear 150 by interlocking with the horizontal long hole 172 (or while generating a torsional stress for a 360° rotation) when the second gear 150 rotates by the rotational energy received from the first gear 140.

In addition, the eccentric shaft 152 causes the housing 170 to move up/down vertically as a torsional stress is generated as the eccentric shaft 152 and the horizontal long hole 172 are twisted in the process of being connected with the horizontal long hole 172.

It is preferable that the eccentric shaft 152 is provided asymmetrically on the second gear 150 so as not to coincide with the center of the second gear 150.

Meanwhile, a gear ratio of the first gear 140 and the second gear 150 of the present disclosure is implemented as 1:2, but this is not limited thereto, and may change to 1:1, 1:1.5, etc. by those skilled in the art according to the purpose and use.

The first transducer assembly 160 of the present disclosure is coupled with the housing 170, so that it may vertically move up/down from a starting position by following the up/down vertical movement of the housing 170.

The housing 170 of the present disclosure may have the ball screw 120 penetrated to both sides for the horizontal movement of the first transducer assembly 160.

In addition, the inside space of the housing 170 may be provided with a box module 171 for boxing the ball nut 130, the first gear 140, and the second gear 150 into a single module form, as illustrated in FIG. 6B.

The box module 171 may box the ball nut 130, the first gear 140, and the second gear 150 into a single module form so that the ball nut 130, the first gear 140, and the second gear 150 may move horizontally along the ball screw 120 as one unit.

That is, the housing 170 may move horizontally through the box module 171, and the first transducer assembly 160 may move horizontally by being coupled with the housing 170 and following the horizontal movement of the housing 170.

In addition, the housing 170 may have a horizontal long hole 172 formed on the side portion through which the eccentric shaft 152 provided in the second gear 150 penetrates, as illustrated in FIG. 6B, for the horizontal movement and up/down vertical movement of the first transducer assembly 160.

The horizontal long hole 172 is a horizontal long hole that causes the penetrated eccentric shaft 152 to generate the torsional stress for 360° rotation of the second gear 150 when the second gear 150 rotates by the first gear 140, thereby allowing the first transducer assembly 160 to vertically move up/down along the housing 170 in which the horizontal long hole 172 is formed.

In addition, the housing 170 may have a vertical long hole 173 formed in the side portion through which the ball screw 120 penetrates, as illustrated in FIG. 5.

The vertical long hole 173 is a vertical long hole that prevents the interference of the ball screw 120 during the up/down vertical movement process of the housing 170 for vertically moving the first transducer assembly 160 up/down.

In addition, the housing 170 may be coupled with the first transducer assembly 160 at one side portion 174, which is the lower side portion, based on FIG. 6B so that the horizontal movement and up/down vertical movement of the first transducer assembly 160 are implemented.

The first transducer assembly 160 of the present disclosure is coupled to the housing 170 through one side portion 174, so that the first transducer assembly 160 may move horizontally and vertically move up/down by following the horizontal movement and up/down vertical movement of the housing 170.

As illustrated in FIG. 2, as the eccentric shaft 152 is biased to one side in the internal space of the housing 170 to penetrate through the horizontal long hole 172, to prevent the focus of the focused ultrasound irradiated to the skin of the subject from changing due to vibration generated during the up/down vertical movement of the first transducer assembly 160, the structure 100 of the present disclosure may further have an up/down vertical movement auxiliary means 180 provided on the other side of the housing 170 to assist the up/down vertical movement of the first transducer assembly 160.

In addition, the up/down vertical movement auxiliary means 180 may correct the imbalance of the first transducer assembly 160 together with the second gear 150 to enable more balanced and stable operation, thereby securing the structural stability and improving the overall durability of the structure 100 itself.

Referring to FIG. 2, the up/down vertical movement auxiliary means 180 of the present disclosure may include a rotating shaft 181, a rotary member 182, and an auxiliary eccentric shaft 183.

The rotating shaft 181 may be connected to the second gear 150, which rotates by receiving the rotational force of the first gear 140, and may receive the rotational energy of the second gear 150.

The rotary member 182 may be connected to the rotating shaft 181 and may receive the rotational energy from the second gear 150 through the rotating shaft 181.

The rotary member 182 may have a gear ratio of 1:1 with respect to the second gear 150.

The auxiliary eccentric shaft 183 is provided asymmetrically on the rotary member 182 so as not to coincide with the center of the rotary member 182, and may convert the rotational energy of the rotary member 182 into the up/down movement energy while interfering with the rotation of the rotary member 182 (or while generating the torsional stress for 360° rotation) when the rotary member 182 rotates by the rotational energy of the second gear 150 transmitted through the rotating shaft 181.

Meanwhile, the housing 170 may be formed with other horizontal long holes when the horizontal long hole 172 through which the eccentric shaft 152 penetrates is the first horizontal long hole 172. Preferably, a second long hole (not illustrated) through which the auxiliary eccentric shaft 183 penetrates may be formed on the side portion.

That is, the auxiliary eccentric shaft 183 may penetrate through the second horizontal long hole (not illustrated) of the housing 170, and may convert the rotational energy of the rotary member 182 into the up/down movement energy while interfering with the rotation of the rotary member 182 (or while generating the torsional stress for 360° rotation) by interlocking with the second horizontal long hole (not illustrated).

In this way, the first transducer assembly 160 of the present disclosure may vertically move up/down stably in a more balanced manner through the second gear 150 and the up/down vertical movement auxiliary means 180.

However, since the structure 100 of the present disclosure enables the up/down vertical movement of the first transducer assembly 160 through the second gear 150, the up/down vertical movement auxiliary means 180 may be omitted from the components for cost reduction and simplification of configuration.

In addition, when the up/down vertical movement auxiliary means 180 is omitted, the eccentric shaft 152 may be separated from the horizontal long hole 172 depending on the degree of horizontal movement of the box module 171 when the box module 171 horizontally moves in a direction away from the horizontal long hole 172, so a width (horizontal width) of the housing 170 may be reduced compared to FIG. 2 in order to reduce the horizontal movement range of the box module 171.

Hereinafter, the horizontal movement and the up/down vertical movement of the first transducer assembly 160 will be described in detail with reference to FIG. 6, based on the state where the up/down vertical movement auxiliary means 180 is omitted from the components.

Referring to FIGS. 6A and 6B, the horizontal movement of the first transducer assembly 160 means that the housing 170 moves parallel to a longitudinal direction based on the longitudinal direction in which the ball screw 120 extends through the box module 171 inside.

Here, the horizontal movement of the first transducer assembly 160 may be implemented based on the fact that the ball nut 130 moves linearly by following the rotation of the ball screw 120 and the first gear 140 engaging with the ball nut 130 follows the linear movement of the ball nut 130.

The first transducer assembly 160 may horizontally move by the pitch distance of the ball screw 120 based on the fact that the ball nut 130 and the first gear 140 move linearly to one side by the pitch distance of the ball screw 120 during the horizontal movement process.

Referring to FIGS. 6A and 6B, the up/down vertical movement of the first transducer assembly 160 means that the housing 170 reciprocates in a width direction crossing the longitudinal direction in which the ball screw 120 extends.

Here, the up/down vertical movement of the first transducer assembly 160 may be implemented based on the fact that the ball nut 130, the first gear 140, and the second gear 150 are boxed into the internal space of the housing 170 through the box module 171, the first gear 140 is fitted into the accommodation groove 122 of the ball screw 120 through the protrusion 142 to follow the rotation of the ball screw 120, and the second gear 150 receives the rotational energy from the first gear 140, and the eccentric shaft 152 of the second gear 150 and the horizontal long hole 172 of the housing 170 are interlocked to convert the rotational energy of the second gear 150 into the up/down movement energy while interfering with the rotation of the second gear 150 (or generating the torsional stress for 360° rotation).

The first transducer assembly 160 may repeat the up/down vertical movement based on the up/down movement energy converted through the interlocking between the eccentric shaft 152 and the horizontal long hole 172 during the up/down vertical movement process.

In addition, the eccentric shaft 152 moves within the horizontal long hole 172 as illustrated in FIG. 6B when interfering with the rotation of the second gear 150 together with the horizontal long hole 172 for the up/down vertical movement of the first transducer assembly 160, and when moving to the first position 152a, may move the housing 170 upward, and when moving to the second position 152b, move the housing 170 further upward.

The first transducer assembly 160 of the present disclosure may move horizontally and up/down vertically along a path in an example illustrated in FIG. 6C while performing treatment on the skin of the subject using the surgical device that irradiates the focused ultrasound.

Referring to FIG. 6C, the first transducer assembly 160 may be disposed at starting position a to perform the treatment on the skin of the subject using the surgical device that irradiates the focused ultrasound.

In this case, the starting position a may be a midpoint of a maximum upper point at which the first transducer assembly 160 can vertically move upward and a maximum lower point at which the first transducer assembly 160 can vertically move downward during the up/down vertical movement process.

In addition, the fact that the first transducer assembly 160 is disposed at the starting position a means that a lower end of the first transducer assembly 160 is disposed at coordinates corresponding to the starting position a based on FIG. 2.

In this way, the first transducer assembly 160 disposed at the starting position a may move horizontally to one side by the pitch distance of the ball screw 120 while the skin of the subject is treated using the surgical device, and at the same time, may primarily vertically move upward from the starting position a to the second upper point c via the first upper point b for irradiating the focused ultrasound by the interlocking between the eccentric shaft 152 and the horizontal long hole 172.

In this case, the surgical device may irradiate the focused ultrasound to the skin of the subject at the first upper point b and the second upper point c, or may be disposed at the first upper point b or the second upper point c and then irradiate the focused ultrasound to the skin of the subject, according to the purpose of the treatment using the focused ultrasound.

In addition, when the surgical device irradiates the focused ultrasound to the skin of the subject at the first upper point b and the second upper point c, respectively, the surgical device irradiates the focused ultrasound to the skin of the subject to multiple depths from the starting position a until the primary upward vertical movement is completed, thereby improving the skin condition of the subject.

In addition, the second upper point c may be the maximum upper point that the first transducer assembly 160 may vertically move upward based on the upward movement energy transmitted from the eccentric shaft 152.

Referring back to FIG. 6C, the first transducer assembly 160, which has primarily completed the upward vertical movement, may primarily move downward vertically from the second upper point c to a second lower point e via a first lower point d for irradiating the focused ultrasound by the interlocking between the eccentric shaft 152 and the horizontal long hole 172 while continuing the horizontal movement to one side.

In this case, the surgical device may irradiate the focused ultrasound to the skin of the subject at the first lower point d and the second lower point e, or may be disposed at the first lower point d or the second lower point e and then irradiate the focused ultrasound to the skin of the subject, according to the purpose of the treatment using the focused ultrasound.

In addition, when the surgical device irradiates the focused ultrasound to the skin of the subject at the first lower point d and the second lower point e, respectively, the surgical device may irradiate the focused ultrasound to the skin of the subject to multiple depths from the second upper point c until the primary downward vertical movement is completed, thereby improving the skin condition of the subject.

The first lower point d may be a point at the same height as the first upper point b, and the second lower point e may be a point at the same height as the starting position a.

Referring back to FIG. 6C, the first transducer assembly 160, which has primarily completed the downward vertical movement, may secondarily move downward vertically from the second lower point e to a fourth lower point g via a third lower point f for irradiating the focused ultrasound by the interlocking between the eccentric shaft 152 and the horizontal long hole 172 while continuing the horizontal movement to one side.

In this case, the surgical device may irradiate the focused ultrasound to the skin of the subject at the third lower point f and the fourth lower point g, or may be disposed at the third lower point f or the fourth lower point e and then irradiate the focused ultrasound to the skin of the subject, according to the purpose of the treatment using the focused ultrasound.

In addition, when the surgical device irradiates the focused ultrasound to the skin of the subject at the third lower point f and the fourth lower point g, respectively, the surgical device may irradiate the focused ultrasound to the skin of the subject to multiple depths from the second lower point e until the secondary downward movement is completed, thereby improving the skin condition of the subject.

In addition, the fourth lower point g may be the maximum upper point that the first transducer assembly 160 may vertically move downward based on the downward movement energy transmitted from the eccentric shaft 152.

Referring back to FIG. 6C, the first transducer assembly 160, which is secondarily completed the downward vertical movement, may secondary move upward vertically from the fourth lower point g to a fourth upper point i via a third upper point h for irradiating the focused ultrasound by the interlocking between the eccentric shaft 152 and the horizontal long hole 172 while continuing the horizontal movement to one side.

In this case, the surgical device may irradiate the focused ultrasound to the skin of the subject at a third upper point h and the fourth upper point i, or may be disposed at the third upper point h or the fourth upper point i and then irradiate the focused ultrasound to the skin of the subject, according to the purpose of the treatment using the focused ultrasound.

In addition, when the surgical device irradiates the focused ultrasound to the skin of the subject at the third upper point h and the fourth upper point i, respectively, the surgical device may irradiate the focused ultrasound to the skin of the subject to multiple depths from the fourth lower point g until the secondary upward movement is completed, thereby improving the skin condition of the subject.

The third upper point h may be a point at the same height as the third lower point f, and the fourth upper point i may be a point at the same height as the starting position a.

Referring back to FIG. 6C, the first transducer assembly 160, which has secondarily completed the upward vertical movement, may tertiarily move upward vertically from the fourth upper point i to a sixth upper point k via a fifth upper point j for irradiating the focused ultrasound by the interlocking between the eccentric shaft 152 and the horizontal long hole 172 while continuing the horizontal movement to one side.

In this case, the surgical device may irradiate the focused ultrasound to the skin of the subject at the fifth upper point j and the sixth upper point k, or may be disposed at the fifth upper point j or the sixth upper point k and then irradiate the focused ultrasound to the skin of the subject, according to the purpose of the treatment using the focused ultrasound.

In addition, when the surgical device irradiates the focused ultrasound to the skin of the subject at the fifth upper point j and the sixth upper point k, respectively, the surgical device may irradiate the focused ultrasound to the skin of the subject to multiple depths from the fourth upper point i until the tertiarily upward vertical movement is completed, thereby improving the skin condition of the subject.

The fifth upper point j may be a point at the same height as the first upper point b, and the sixth upper point k may be a point at the same height as the second upper point c which is the maximum upper point where the first transducer assembly 160 can vertically move upward based on the upward movement energy transmitted from the eccentric shaft 152.

In an exemplary embodiment, the up/down vertical movement process of the first transducer assembly 160 may be a process that proceeds in the order of primary upward vertical movement—primary and secondary downward vertical movement—secondary and tertiarily upward vertical movement . . . from the starting position a, as if one cycle of a sine wave is repeated, and then returns to the starting position a when the skin treatment of the subject ends.

That is, the first transducer assembly 160 moves horizontally to one side by the pitch distance of the ball screw 120 and at the same time primarily moves upward vertically from the starting position a during the first vertical movement while the skin treatment of the subject is in progress, and from then on, the first transducer assembly 160 may repeat the downward vertical movement and the upward vertical movement twice until the skin treatment of the subject using the surgical device ends, so that the focused ultrasound is irradiated to the skin of the subject at multiple depths, and when the skin treatment of the subject ends, the first transducer assembly may return to the starting position a.

As a specific example, the up/down vertical movement process of the first transducer assembly 160 may be a process in which, assuming that the skin penetration depth of the focused ultrasound irradiated from the surgical device is 3 mm at the starting position a, the skin penetration depth of the focused ultrasound may change from 3 mm to 1 mm during the primary upward vertical movement, the skin penetration depth of the focused ultrasound may change from 1 mm to 5 mm during the primary and secondary downward vertical movements, and the skin penetration depth of the focused ultrasound may change from 5 mm to 1 mm during the second and third upward vertical movements, and when the skin treatment of the subject ends, the process returns to the starting position a.

However, in the up/down vertical movement process of the first transducer assembly 160, the first vertical movement from the starting position a is not limited to the upward vertical movement as illustrated in FIG. 6C, and on the contrary, may proceed from the downward vertical movement.

In this case, the up/down vertical movement process of the first transducer assembly 160 may be a process that proceeds in the order of the primary downward vertical movement—primary and secondary upward vertical movement—secondary and tertiarily downward vertical movement . . . from the starting position a, and then return to the starting position a when the skin treatment of the subject ends.

In addition, the up/down vertical movement process of the first transducer assembly 160 is not limited to starting from the starting position a, but may proceed in the form of repeating the up/down vertical movement from one of the maximum upper point and the maximum lower point toward the other point.

The up/down vertical movement process of the first transducer assembly 160 may be a process of repeating the up/down vertical movement from the starting position a before the skin treatment of the subject starts, and then returning to the starting position a when the skin treatment of the subject ends.

Meanwhile, the surgical device of the present disclosure may be a device for irradiating the focused ultrasound to the skin of the subject to multiple depths, and may be a cartridge and a handpiece to which the structure 100 can be applied (or can be included).

Here, the handpiece, as a user interface for irradiating the focused ultrasound to the skin of the subject through manipulation of the practitioner, may be a device that a practitioner holds, and the cartridge may be a component that is re-usably and replaceably attached to the handpiece to adjust the focal depth and intensity of the focused ultrasound to be irradiated to the skin of the subject.

In this case, when the structure 100 is applied to the cartridge, the components of the structure 100 except for the motor (not illustrated) and the rotating shaft (not illustrated) of the motor may be built into the cartridge.

In addition, the structure 100 may perform the role of a traction shaft for moving the transducer (not illustrated) using the driving force of the motor (not illustrated) built into the handpiece of the first transducer assembly 160 to irradiate the focused ultrasound generated from the transducer (not illustrated) to multiple depths.

In the present disclosure, the fact that the first transducer assembly 160 uses the driving force of the motor (not illustrated) means that it uses the rotational force of the rotating shaft (not illustrated) of the motor, and the method of using the rotational force of the rotating shaft (not illustrated) of the motor is not limited, but one exemplary embodiment may use the rotational force of the motor (not illustrated) as follows.

As a specific example, the first transducer assembly 160 is not illustrated in the drawings, but the ball screw 120 rotates by receiving the rotational power of the motor (not illustrated) through the interaction between a first friction plate (not illustrated) that is built into the handpiece and receives the rotational power from the rotating shaft (not illustrated) of the motor, and a second friction plate (not illustrated) provided at the end of the ball screw 120, so the housing 170 may horizontally move and vertically move up/down by following the horizontal movement and up/down vertical movement.

Meanwhile, the transducer (not illustrated) may be a device that is built into the cartridge corresponding to the structure 100 built into the handpiece, is coupled to one side of the first transducer assembly 160, and may horizontally move and vertically move up/down by following the horizontal movement and the up/down vertical movement of the first transducer assembly 160 and generate the focused ultrasound and irradiate the focused ultrasound to the skin of the subject while the surgical method is being performed on the skin of the subject.

In addition, although not illustrated in the drawing, the cartridge may have a transmission opening (not illustrated) through which the focused ultrasound passes formed on a contact surface that comes into contact with the skin of the subject so that focused ultrasound generated from the transducer (not illustrated) may be irradiated onto the skin of the subject.

On the other hand, when the structure 100 is applied to the handpiece, the first transducer assembly 160 may be coupled to a second transducer assembly (not illustrated) included in the cartridge while performing the role of the first traction shaft for moving the transducer (not illustrated) by using the driving force of the motor (not illustrated) built into the handpiece.

The second transducer assembly (not illustrated) may be coupled to the first transducer assembly 160 to follow the horizontal movement and the up/down vertical movement of the first transducer assembly 160, thereby performing the role of the second traction shaft for moving the transducer (not illustrated).

Meanwhile, the transducer (not illustrated) may be a device that is built into the cartridge corresponding to the structure 100 built into the handpiece, and is coupled to the second transducer assembly (not illustrated) to horizontally move and vertically move up/down while following the horizontal movement and the up/down vertical movement of the second transducer assembly (not illustrated) and to generate the focused ultrasound while the surgical method is performed on the skin of the subject to irradiate the generated focused ultrasound to the skin of the subject.

Although not illustrated in the drawings, the handpiece may have an engaging opening (not illustrated) having a movable diameter formed on the binding surface of the cartridge through which the first transducer assembly 160 or the second transducer assembly (not illustrated) may penetrate so that the first transducer assembly 160 may move and may be coupled to the second transducer assembly (not illustrated) included in the cartridge.

In addition, the cartridge may have a transmission opening (not illustrated) formed through which the focused ultrasound passes when the structure 100 is applied to the handpiece, just as when it is applied to the cartridge.

Meanwhile, although not illustrated in the drawing, the surgical device of the present disclosure may be equipped with an encoder that measures a rotation angle of the motor 110.

In addition, the handpiece 11 implemented in a wired or wireless manner may be provided with the display unit (not illustrated) that visually displays the rotation angle of the motor 110 measured by the encoder.

However, the display unit is not limited to being provided in the handpiece 11 and may be a component provided in a separate output device (not illustrated) connected to the handpiece 11 when the handpiece 11 is implemented as a wired device.

In this case, measuring the rotation angle of the motor 110 in the encoder is to accurately calculate position coordinates X and Y of the first transducer assembly 160.

More specifically, the encoder accurately synchronizes the horizontal movement and the up/down vertical movement of the first transducer assembly 160 with the rotation angle of the ball screw 120 in the structure of the structure 100, the ball screw 120 may be accurately synchronized with the motor 110 as it rotates by the power of the motor 110, so that the position coordinates X and Y of the first transducer assembly 160 may be accurately calculated based on the rotation angle of the motor 110.

In addition, the display unit may visually display not only the rotation angle of the motor 110 but also the position coordinates X and Y of the first transducer assembly 160.

In this way, since a surgical device provided with an encoder may accurately calculate the position coordinates X and Y of the first transducer assembly 160, the surgical device may irradiate the focused ultrasound to the skin of the subject to multiple depths at a desired location while a sinusoidal path based on the horizontal movement and the up/down vertical movement of the first transducer assembly 160 is performed according to the manipulation of the practitioner.

Surgical Method

Hereinafter, the process of the surgical method (S100) using the structure 100 of the present disclosure will be described in detail with reference to the accompanying drawings, and the structure 100 will be based on the form in which the up/down vertical movement auxiliary means 180 is excluded from the components.

Figure 7:
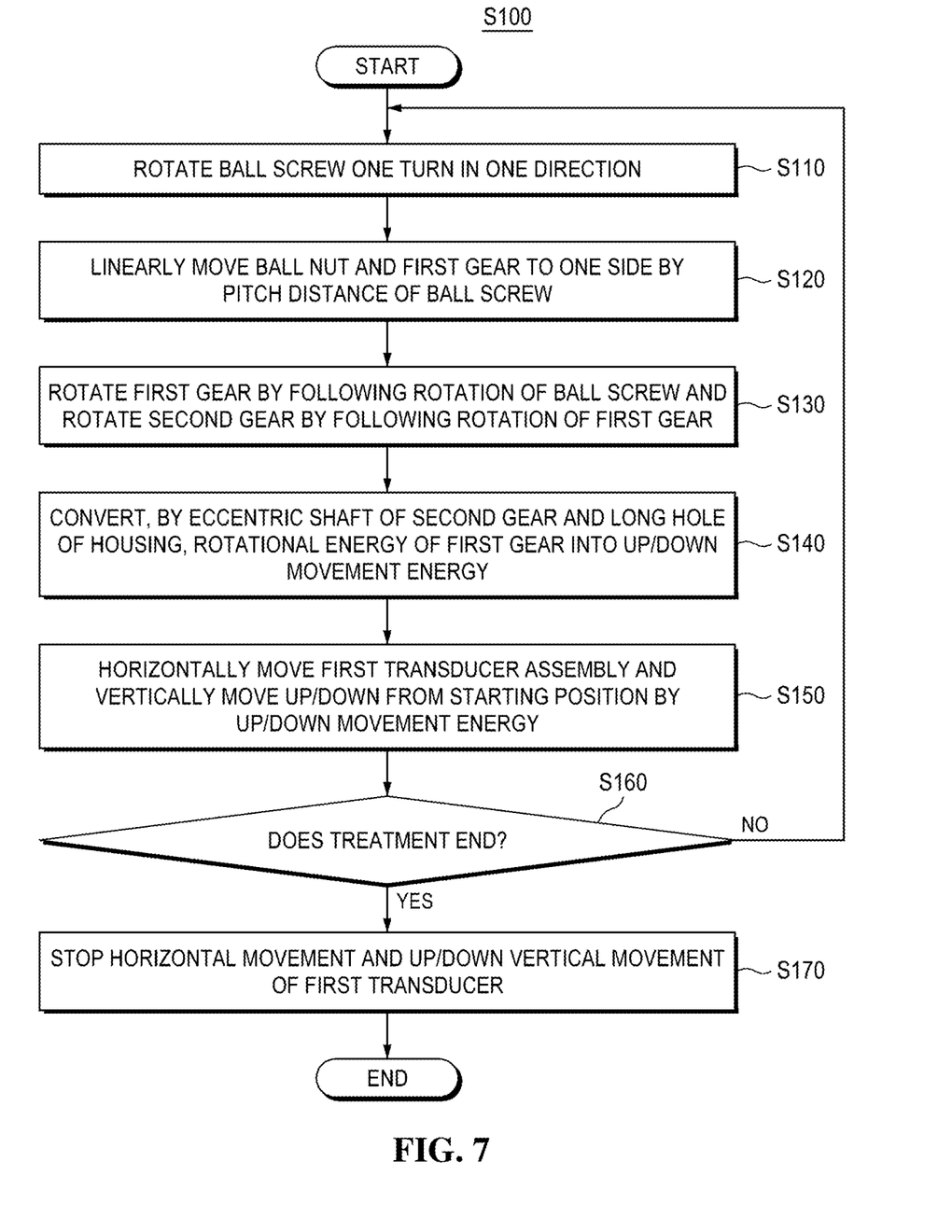
FIG. 7 is a flowchart illustrating a process of a surgical method using a structure of a surgical device for irradiating focused ultrasound to multiple depths according to an exemplary embodiment of the present disclosure.

FIG. 7 is a flowchart illustrating a process of a surgical method using a structure of a surgical device for irradiating focused ultrasound to multiple depths according to an exemplary embodiment of the present disclosure.

Referring to FIG. 7, the surgical method (S100) of the present disclosure is a treatment process for improving the skin condition of the subject by irradiating the focused ultrasound to multiple depths, and may be performed in the following order from the start to the end of the skin treatment of the subject: a ball screw rotation step (S110), a linear movement step (S120), a first gear and second gear rotation step (S130), an up/down movement energy conversion step (S140), a horizontal movement and up/down vertical movement step (S150), a step for determining whether the treatment ends (S160), and a horizontal movement and up/down vertical movement stop step (S170).

In the ball screw rotation step (S110), the ball screw 120 may rotate one turn in one direction by the power of the motor 110 equipped with a rotating shaft.

In the linear movement step (S120), the ball nut 130 moves linearly along the ball screw 120, and the first gear 140 follows the linear movement of the ball nut 130, so that the ball nut 130 and the first gear 140 may move linearly to one side by the pitch distance of the ball screw 120.

In the first gear and second gear rotation step (S130), the first gear 140 rotates by following the rotation of the ball screw 120, and the second gear 150 that meshes with the first gear 140 may rotate by following the rotation of the first gear 140.

In the first gear and second gear rotation step (S130), the rotation of the second gear 150 may occur according to the interlocking of the eccentric shaft 152 and the horizontal long hole 172.

In addition, the linear movement step (S120) and the first and second gear rotation step (S130) may be performed simultaneously.

In the up/down movement energy conversion step (S140), the eccentric shaft 152 of the second gear 150 and the horizontal long hole 172 of the housing 170 may convert the rotational energy of the second gear 150 into the up/down movement energy for the up/down vertical movement of the first transducer assembly 160 while interfering with the rotation of the second gear 150 (or while generating the torsional stress for 360° rotation).

In this case, the linear movement step (S120), the first and second gear rotation step (S130), and the up/down movement energy conversion step (S140) may be performed simultaneously.

In the horizontal movement and up/down vertical movement step (S150), the first transducer assembly 160 may horizontally move to one side based on the linear movement of the ball nut 130 and the first gear 140 along the housing 170, and may vertically move up/down based on the interlocking of the eccentric shaft 152 and the horizontal long hole 172 while horizontally moving.

In the horizontal movement and up/down vertical movement step (S150), the surgical device may horizontally move to one side based on the horizontal movement and up/down vertical movement of the first transducer assembly 160 and simultaneously irradiate the skin of the subject with the focused ultrasound to multiple depths.

Meanwhile, the practitioner may determine whether the skin treatment of the subject ends while the steps (S110 to S150) of the surgical method (S100) of the present disclosure are in progress (S160).

In this case, when the practitioner determines that the skin treatment of the subject does not end (S160—NO), the surgical method (S100) of the present disclosure may repeat the steps (S110 to S150).

On the other hand, when the practitioner determines that the skin treatment of the subject ends (S160—YES), the first transducer assembly 160 stops the horizontal movement and the up/down vertical movement (S170), and the skin treatment of the subject may end by returning the first transducer assembly 160 to the starting position.

Effects of Present Disclosure

According to the present disclosure, it is possible to provide the surgical device of a simple configuration including the structure 100 capable of adjusting the irradiation depth of the focused ultrasound by implementing the up/down vertical movement of the transducer assembly 160 while omitting the configuration of the actuator for horizontal movement and up/down vertical movement, and setting the irradiation depth of the focused ultrasound without adding the separate sensor.

In addition, according to the present disclosure, the structure 100 irradiates the focused ultrasound to the skin of the subject to multiple depths while the transducer assembly 160 moves horizontally and up/down vertically while accommodating the conventional surgical method, so it is possible to improve the skin condition of the subject based on various surgical methods.

A detailed description of preferred exemplary embodiments of the present disclosure disclosed as described above is provided to enable a person skilled in the art to implement or practice the present disclosure. Although exemplary embodiments of the present disclosure have been disclosed above, it may be understood by those skilled in the art that the present disclosure may be variously modified and changed without departing from the scope of the present disclosure. For example, a person skilled in the art may use each configuration described in the above-described exemplary embodiments by combining them with each other. Accordingly, the present disclosure is not intended to be limited to the exemplary embodiments illustrated herein but is to be given the widest scope consistent with the principles and novel features disclosed herein.

The present disclosure may be implemented in another specific form without departing from the spirit and the essential feature of the present disclosure. Therefore, the above-mentioned detailed description is to be interpreted as being illustrative rather than being restrictive in all aspects. The scope of the present disclosure is to be determined by reasonable interpretation of the claims, and all modifications within an equivalent range of the present disclosure fall in the scope of the present disclosure. The present disclosure is not intended to be limited to the exemplary embodiments illustrated herein but is to be given the widest scope consistent with the principles and novel features disclosed herein. In addition, claims that do not have an explicit reference relationship in the patent claims can be combined to form an exemplary embodiment or can be included as a new claim through amendment after filing.

What is claimed is:

1. A structure of a surgical device for irradiating focused ultrasound to multiple depths, the structure built into the surgical device comprising:
   a motor equipped with a rotating shaft;
   a ball screw rotating by power of the motor, having a first external screw thread engraved on an outer side, and having an accommodation groove formed in a longitudinal direction on a portion of the outer side;
   a ball nut having an internal screw thread engraved on an inner side that meshes with the first external screw thread when the ball screw is penetrated, and moving linearly by following rotation of the ball screw;
   a first gear having a protrusion formed on an inner side that is fitted into the accommodation groove when the ball screw is penetrated to follow the rotation of the ball screw, engaging with the ball nut to follow a linear movement of the ball nut, and having a second external screw thread engraved on an outer diameter;
   a second gear having a third external screw thread engraved on an outer diameter and meshing with the second external screw thread to follow the rotation of the first gear, and having an eccentric shaft provided asymmetrically;
   a first transducer assembly moving horizontally by linear movement of the ball nut and the first gear, and vertically moving up/down to irradiate the focused ultrasound to the multiple depths; and
   a housing formed with a horizontal long hole that is coupled with the first transducer assembly while boxing the ball nut, the first gear, and the second gear and converts rotational energy of the second gear into up/down movement energy for vertically moving the first transducer assembly up/down while interfering with the rotation of the second gear by interlocking with the eccentric shaft.

2. The structure according to claim 1, wherein the first transducer assembly moves horizontally to one side by a pitch distance of the ball screw based on the fact that the ball nut and the first gear move linearly to one side by the pitch distance of the ball screw when the ball screw rotates one turn in one direction.

3. The structure according to claim 2, wherein, while the first transducer assembly moves horizontally to one side by the pitch distance of the ball screw, the first transducer assembly repeats an up/down vertical movement from one point of a maximum upper point and a maximum lower point toward the other point in a form that one cycle of a sine wave is repeated through the up/down movement energy converted from the rotational energy of the second gear based on the interlocking between the eccentric shaft and the horizontal long hole.

4. The structure according to claim 3, wherein the first transducer assembly repeats the up/down vertical movement from a starting position which is a midpoint between the maximum upper point and the maximum lower point before a treatment of a subject starts, and then returns to the starting position when the treatment of the subject ends.

5. The structure according to claim 1, further comprising: an up/down vertical movement auxiliary means assisting an up/down movement of the first transducer assembly.

6. The structure according to claim 5, wherein the up/down vertical movement auxiliary means is connected to the second gear to receive the rotational energy from the second gear, and converts the rotational energy of the second gear for vertically moving the first transducer assembly up/down into the up/down movement energy by interlocking with the housing.

7. The structure according to claim 6, wherein the housing has a horizontal long hole additionally formed on a side portion opposite to a side portion where the horizontal long hole is formed.

8. The structure according to claim 7, wherein the up/down vertical movement auxiliary means includes:
- a rotating shaft connected to the second gear to receive the rotational energy from the second gear;
- a rotary member connected to the rotating shaft to receive the rotational energy from the second gear through the rotating shaft; and
- an auxiliary eccentric shaft asymmetrically provided on the rotary member, and penetrating through the horizontal long hole additionally formed in the housing to convert the rotational energy of the rotary member into the up/down movement energy while interfering with the rotation of the rotary member when the rotary member rotates by the rotational energy of the second gear.

9. The structure according to claim 1, wherein the surgical device is a cartridge and a handpiece to which the structure is applicable.

10. The structure according to claim 9, wherein, when the structure is applied to the cartridge, the first transducer assembly performs a role of a traction shaft for moving a transducer that irradiates the focused ultrasound using driving force of the motor built into the handpiece, and
the transducer is built into the cartridge, coupled with the first transducer assembly, and follows the horizontal movement and the up/down vertical movement of the first transducer assembly to move horizontally and vertically move up/down and irradiate the focused ultrasound to the multiple depths.

11. The structure according to claim 9, wherein, when the structure is applied to the handpiece, the first transducer assembly is coupled with a second transducer assembly included in the cartridge while performing a role of a first traction shaft for moving the transducer that irradiates the focused ultrasound using driving force of the motor built into the handpiece,
the second transducer assembly performs a role of a second traction shaft for moving the transducer by following the horizontal movement and the up/down vertical movement of the first transducer assembly, and
the transducer is built into the cartridge, coupled with the second transducer assembly, and follows the horizontal movement and the up/down vertical movement of the second transducer assembly to move horizontally and vertically move up/down and irradiate the focused ultrasound to the multiple depths.

12. The structure according to claim 10, wherein the cartridge has a penetration opening, through which the focused ultrasound passes, formed on a contact surface that contacts the skin of the subject so that the focused ultrasound generated from the transducer is irradiated to the skin of the subject.

13. The structure according to claim 11, wherein the handpiece has an engaging opening having a movable diameter, through which the first transducer assembly or the second transducer assembly penetrates, formed on a binding surface with the cartridge so that the first transducer assembly moves and is coupled with the second transducer assembly.

14. The structure according to claim 1, wherein the housing has a vertical long hole formed in a side portion, through which the ball screw penetrates, to prevent the interference of the ball screw during an up/down vertical movement of the first transducer assembly.

15. A surgical method using a structure of a surgical device for irradiating focused ultrasound to multiple depths, the surgical method using the structure built into the surgical device comprising:
a) rotating a ball screw one turn in one direction by power of a motor equipped with a rotating shaft;
b) moving a ball nut linearly along the ball screw and allowing a first gear engaging with the ball nut to follow linear movement of the ball nut so that the ball nut and the first gear move linearly to one side by a pitch distance of the ball screw;
c) simultaneously with step b), rotating the first gear by following the rotation of the ball screw and rotating a second gear meshed with the first gear by following the rotation of the first gear;
d) simultaneously with step c), converting rotational energy of the second gear into up/down movement energy for vertically moving up/down a first transducer assembly while an eccentric shaft of the second gear and a horizontal long hole of the housing interfere with the rotation of the second gear; and
e) horizontally moving the first transducer assembly along the housing while repeating steps a to d) and vertically moving the first transducer assembly up/down to irradiate the focused ultrasound to the multiple depths by the up/down movement energy.

* * * * *